(12) United States Patent
Keswarpu et al.

(10) Patent No.: US 9,149,646 B2
(45) Date of Patent: Oct. 6, 2015

(54) METHOD AND APPARATUS FOR CONTROLLING A PROCESS OF INJURY THERAPY

(75) Inventors: Payal Keswarpu, Bangalore (IN); Balakrishnan Srinivasan, Bangalore (IN); Srinivas Rao Kudavelly, Bangalore (IN)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 1095 days.

(21) Appl. No.: 13/142,362

(22) PCT Filed: Dec. 22, 2009

(86) PCT No.: PCT/IB2009/055893
§ 371 (c)(1),
(2), (4) Date: Sep. 27, 2011

(87) PCT Pub. No.: WO2010/076737
PCT Pub. Date: Jul. 8, 2010

(65) Prior Publication Data
US 2012/0010683 A1    Jan. 12, 2012

(30) Foreign Application Priority Data
Dec. 31, 2008  (CN) .......................... 2008 1 0190333

(51) Int. Cl.
*A61N 5/06*    (2006.01)
*A61B 5/00*    (2006.01)
*A61B 5/04*    (2006.01)
*A61B 17/00*   (2006.01)

(52) U.S. Cl.
CPC ................ *A61N 5/06* (2013.01); *A61B 5/0059* (2013.01); *A61B 5/04005* (2013.01); *A61B 2017/00061* (2013.01); *A61N 2005/0659* (2013.01)

(58) Field of Classification Search
USPC ........................................ 607/88–90; 205/781
See application file for complete search history.

(56) References Cited

U.S. PATENT DOCUMENTS

| | | | |
|---|---|---|---|
| 4,139,348 A | 2/1979 | Swartz | |
| 7,090,648 B2 | 8/2006 | Sackner | |
| 7,150,710 B2 | 12/2006 | Haber | |
| 2004/0092812 A1* | 5/2004 | Jones et al. | ......... 600/420 |
| 2004/0111016 A1 | 6/2004 | Casscells | |
| 2004/0254419 A1 | 12/2004 | Wang | |
| 2006/0074282 A1 | 4/2006 | Ward | |
| 2007/0129776 A1 | 6/2007 | Robins | |
| 2010/0331928 A1* | 12/2010 | Dunning et al. | ........ 607/88 |

FOREIGN PATENT DOCUMENTS

| | | | |
|---|---|---|---|
| WO | 0174252 A2 | 10/2001 | |
| WO | 2007144810 A1 | 12/2007 | |
| WO | 2008137737 A2 | 11/2008 | |

OTHER PUBLICATIONS

Martin, Felipe A. et al "Simultaneous Monitoring of Nitric Oxide, Oxyhemoglobin and Deoxyhemoblobin from Small Areas of the Rat Brain by in Vivo Visible Spectroscopy and a Least-Square Approach" Journal of Neuroscience Methods, vol. 140, 2004, pp. 75-80.

* cited by examiner

*Primary Examiner* — William Thomson
*Assistant Examiner* — Jeffrey Lipitz

(57) ABSTRACT

A method and apparatus for controlling a process of injury therapy includes monitoring a Nitric Oxide level of the injury, generating a controlling signal by comparing the Nitric oxide level with a predefined threshold, and adjusting a dosage of light for the injury therapy according to the controlling signal.

18 Claims, 3 Drawing Sheets

METHOD AND APPARATUS FOR CONTROLLING A PROCESS OF INJURY THERAPY

FIELD OF THE INVENTION

The invention relates to a method and apparatus for controlling a process of injury therapy.

BACKGROUND OF THE INVENTION

Pain is a debilitating effect due to any injury. Also pain in the joints causes serious disability affecting the daily chores and productivity, especially, Osteoarthritis contributes to pain of joints in most of the elderly people.

To reduce pain, the drug therapy, like capsaicin cream, acetaminophen, Non-Steroidal Anti-Inflammatory Drugs (NSAIDs) are prescribed to reduce pain temporarily, but serious side effects are associated. Physical therapy, such as spa, massage, acupuncture and chiropractic manipulation, can help relieve pain for a short duration, but are usually expensive and require skilled personnel.

Currently, in physical therapy field, light therapy system is quite popular. However, during light therapy, the intensity/dosage of light can be adjusted only by intermittent switching on and off the light therapy system manually, which is not convenient and accurate.

SUMMARY OF THE INVENTION

An object of this invention is to provide a method for controlling a process of injury therapy.

The invention provides a method of controlling the process of injury therapy, and the method comprises the steps of:
  monitoring a Nitric Oxide level of the injury,
  generating a controlling signal by comparing the Nitric Oxide level with a predefined threshold, and
  adjusting a dosage of light for the injury therapy according to the controlling signal.

Based on the method of the invention, it is more accurate and convenient to adjust the dosage of injury therapy with minimal side effects.

The invention also provides an apparatus for implementing the steps of the method as mentioned above.

Detailed explanations and other aspects of the invention will be given below.

DESCRIPTION OF THE DRAWINGS

The above and other objects and features of the present invention will become more apparent from the following detailed description considered in connection with the accompanying drawings, in which.

The same reference numerals are used to denote similar parts throughout the figures.

DETAILED DESCRIPTION

Figure 1:
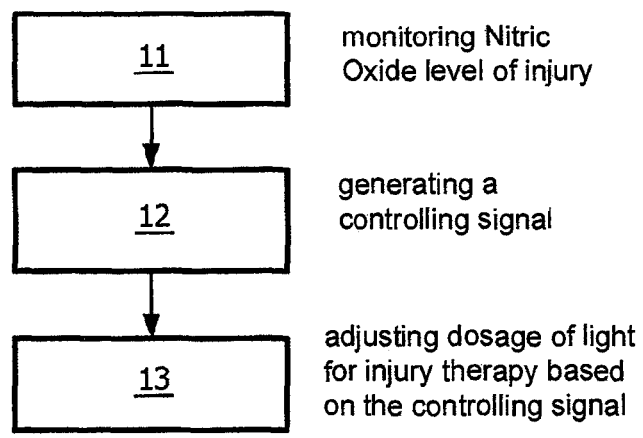
FIG. 1 is a schematic diagram for illustrating an embodiment of the method according to the invention.

FIG. 1 is a schematic diagram for illustrating an embodiment of the method according to the invention. The method of controlling the process of injury therapy comprises the following steps:

monitoring 11 a Nitric Oxide level of the injury,
generating 12 a controlling signal by comparing the Nitric Oxide level with a predefined threshold, and
adjusting 13 a dosage of light for the injury therapy according to the controlling signal.

Light for injury therapy may be Monochromatic infrared light having a wavelength of 890 nm. When light is applied at a surface of an injury, light is absorbed into blood vessels and stimulates the production of Nitric Oxide at the site of injury by the beneficial cNOS (constitutive isoform of Nitric Oxide Synthase) pathway. Nitric Oxide is produced from amino acid called L-Arginine by action of the enzyme Nitric Oxide synthase, and the enzyme has different isoforms. cNOS is a key regulator of homeostasis (regulation of blood flow). Nitric Oxide via the beneficial cNOS pathway is decreased at the site of the injury. It is also well known that in the case of joints affected by Osteoarthritis, Nitric Oxide via the beneficial cNOS pathway is decreased.

Thus, Nitric Oxide released from the site of injury is a reasonable indicator for objective assessment of an injury pain. A substantial pain relief is obtained by Nitric Oxide-based intervention without undesirable side effects through increasing circulation, decreasing nerve irritation, and decreasing inflammation in joints. Under physiological conditions, Nitric Oxide reacts with Oxy-hemoglobin to form Meth-hemoglobin at a very high rate, so, the amount of Meth-hemoglobin at the site of injury is proportional to Nitric Oxide.

The controlling signal indicates to increase the dosage of light (or the intensity of light), if the Nitric Oxide level is higher than the predefined threshold; the controlling signal indicates to decrease the dosage of light, if the Nitric Oxide level is lower than the predefined threshold.

The monitoring step 11 is intended to:
  detect a Meth-hemoglobin level,
  calculate the Nitric Oxide level according to a proportional relationship between the Meth-hemoglobin level and the Nitric Oxide level.

Nitric oxide gets associated with Oxy-hemoglobin when dissolved in blood. The Nitric Oxide and Oxy-hemoglobin in blood are converted to Meth-hemoglobin. The most important reactions of Nitric Oxide are with ferrous Hemoproteins, and especially with Oxy-hemoglobin which yields Meth-hemoglobin:

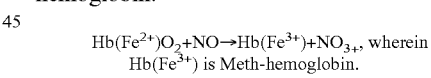

$Hb(Fe^{2+})O_2 + NO \rightarrow Hb(Fe^{3+}) + NO_{3-}$, wherein $Hb(Fe^{3+})$ is Meth-hemoglobin.

Hemoglobin is the quantitatively predominant heme protein in mammals. The primary function of Hemoglobin is to bind, transport, and release molecular oxygen. Hemoglobin bound iron remains in the ferrous state (for example, Oxy-hemoglobin) during oxygen binding, transporting and releasing. When Hemoglobin bound iron is oxidized into ferric iron, the ferric iron cannot transport oxygen. The Oxidized Hemoglobin is called Meth-hemoglobin.

In one embodiment, the Meth-hemoglobin level can be detected by: firstly, detecting a magnetic field formed due to transition from $Fe^{2+}$ to $Fe^{3+}$, and then acquiring a $Fe^{3+}$ level according to the magnetic field, finally calculating the Meth-hemoglobin level according to the $Fe^{3+}$ level.

Measuring the ferric iron ($Fe^{3+}$) can indirectly measure the Meth-hemoglobin. Furthermore, Meth-hemoglobin is proportional to Nitric Oxide, so measuring the ferric iron will measure Nitric Oxide as an indicator of adjusting the dosage of light for injury therapy.

Iron is found in two principle ionic states called ferrous ($Fe^{2+}$) and ferric ($Fe^{3+}$). Magnetism occurs when there is an imbalance in the structural arrangement of the ions. The ferrous ion has a charge of positive two (+2); the ferric ion has a charge of positive three (+3). The two ions have different atomic radii, because the higher charge of the ferric ions pulls the electrons surrounding the ion in tighter, which can lead to electrons that move from the ferrous to the higher positively charged ferric ions, and create a slight magnetic field. The proposed embodiment of the invention measures the magnetic field (also called magnetic flux density, measured in Tesla SI unit).

In another embodiment, the Meth-hemoglobin level can be detected by:

firstly, illuminating a surface (tissue) near the injury. The surface may be illuminated by a specific detecting light source for detecting Meth-hemoglobin, and the specific detecting light source is different from the light source for the injury therapy. The surface may be illuminated by the same light source for the injury therapy. For example, a broadband light source, like the Welch Allyn reflectorized lamp assembly (part number 7103-001), may be used to illuminate the surface near an injury.

secondly, obtaining a spectrum for light reflected from the surface. Oxy-hemoglobin has a absorption spectra at 542 nm and 580 nm, whereas Meth-hemoglobin has a absorption spectra at 630 nm. When Nitric Oxide is released from bound form to diffuse into the surrounding injury, a shift of absorption spectra from 630 nm to 542/580 nm occurs. The reflected light from the surface may be collected by fiber-optic cables and directed towards a micro-spectrometer sensitive to light in the wavelength range (500-700 nm).

thirdly, analyzing a ratio between a Meth-hemoglobin level and an Oxy-hemoglobin level according to the spectrum.

finally, calculating the Meth-hemoglobin level based on the ratio between the Meth-hemoglobin level and the Oxy-hemoglobin level.

In a further embodiment, the Meth-hemoglobin level can be detected by:

firstly, illuminating a surface near the injury. The surface may be illuminated by specific light source used for detection of Meth-hemoglobin, and the specific light source used for detection is different from the light source for the injury therapy. The surface may also be illuminated by the same light source as that used for injury therapy.

secondly, obtaining a wave band of light reflected from the surface.

thirdly, detecting current of light reflected from the surface by converting the light reflected from the surface into current. This can be achieved by a plurality of photodiodes. The photodiodes are predefined as sensitive to three peaks 542 nm, 580 nm and 630 nm.

fourthly, analyzing a ratio between a Meth-hemoglobin level and an Oxy-hemoglobin level according to the current. The Oxy-hemoglobin peaks at 542 nm and 580 nm are identified, and the intensity of Oxy-hemoglobin is compared against the Meth-hemoglobin peak at 630 nm. The ratio of the peaks are then calculated and compared against a predefined model.

finally, calculating the Meth-hemoglobin level based on the ratio between the Meth-hemoglobin level and the Oxy-hemoglobin level.

Figure 2:
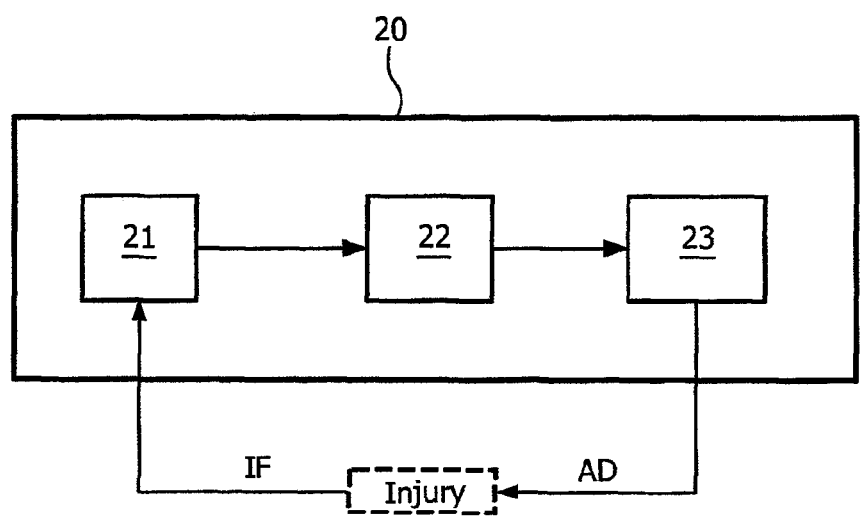
FIG. 2 is a schematic diagram for illustrating an apparatus according to an embodiment of the invention.

FIG. 2 is a schematic diagram for illustrating an apparatus according to an embodiment of the invention. The apparatus for controlling the process of an injury therapy comprises:

a monitoring unit 21 for monitoring a Nitric Oxide level of the injury, a generating unit 22 for generating a controlling signal by comparing the Nitric Oxide level with a predefined threshold, and an adjusting unit 23 for adjusting a dosage of light for the injury therapy according to the controlling signal.

Light for injury therapy may be Monochromatic infrared light having a wavelength of 890 nm. When the light is applied at a surface of an injury, the light is absorbed by the blood and stimulates production of Nitric Oxide in joints by the beneficial cNOS pathway.

Thus, the Nitric Oxide released from an injury is a reasonable indicator for objective assessment of an injury pain. A substantial pain relief is obtained by Nitric Oxide-based intervention without undesirable side effects through increasing circulation, decreasing nerve irritation, and decreasing inflammation in joints.

The controlling signal indicates to increase the dosage, if the Nitric Oxide level is higher than the predefined threshold; the controlling signal indicates to decrease the dosage, if the Nitric Oxide level is lower than the predefined threshold.

The monitoring unit 21 is intended to receive information, shown as IF in FIG. 2, and to monitor the Nitric Oxide level according to the received information. The information may comprise magnetic field information, spectrum information etc. The adjusting unit 23 is intended to output an adjusted dosage of light, shown as AD in FIG. 2.

The monitoring unit 21 is intended to:
detect a Meth-hemoglobin level, and
calculate the Nitric Oxide level according to a proportional relationship between the Meth-hemoglobin level and the Nitric Oxide level.

Under physiological conditions, Nitric Oxide reacts with Oxy-hemoglobin to form Meth-hemoglobin at a very high rate, and so Meth-hemoglobin is proportional to Nitric Oxide.

Nitric oxide gets associated with Oxy-hemoglobin when dissolved in blood. The Nitric Oxide and Oxy-hemoglobin in blood is converted to Meth-hemoglobin. The most important reactions of Nitric Oxide are with ferrous Hemoproteins, and especially with Oxy-hemoglobin which yields Meth-hemoglobin:

$$Hb(Fe^{2+})O_2 + NO \rightarrow Hb(Fe^{3+}) + NO_3{-}, \text{ wherein } Hb(Fe^{3+}) \text{ is Meth-hemoglobin.}$$

Hemoglobin is the quantitatively predominant heme protein in mammals. The primary function of Hemoglobin is to bind, transport, and release molecular oxygen. Hemoglobin bound iron remains in the ferrous state (for example, Oxy-hemoglobin) during oxygen binding, transporting and releasing. When Hemoglobin bound iron is oxidized into ferric iron, the ferric iron cannot transport oxygen. The Oxidized Hemoglobin is called Meth-hemoglobin.

In one embodiment, the monitoring unit 21 may detect the Meth-hemoglobin level by: detecting a magnetic field formed due to transition from $Fe^{2+}$ to $Fe^{3+}$ and then acquiring a $Fe^{3+}$ level according to the magnetic field, finally calculating the Meth-hemoglobin level according to the $Fe^{3+}$ level.

Measuring the ferric iron ($Fe^{3+}$) can indirectly measure the Meth-hemoglobin. Furthermore, Meth-hemoglobin is proportional to Nitric Oxide, and so measuring the ferric iron will measure Nitric Oxide as an indicator of adjusting the dosage of light for injury therapy.

Iron is found in two principle ionic states called ferrous ($Fe^{2+}$) and ferric ($Fe^{3+}$). Magnetism occurs when there is an imbalance in the structural arrangement of the ions. The ferrous ion has charge of positive two (+2); the ferric ion has a charge of positive three (+3). The two ions have different atomic radii because the higher charge of the ferric ions pulls the electrons surrounding the ion in tighter, which can lead to electrons that move from the ferrous to the higher positively charged ferric ions, and create a slight magnetic field. The proposed embodiment of the invention measures the magnetic field (also called magnetic flux density, measured in Tesla SI unit).

In another embodiment, the monitoring unit 21 may be intended to detect the Meth-hemoglobin level by:
  illuminating a surface (tissue) near the injury. The surface may be illuminated by a specific light source used for detecting Meth-hemoglobin, and the specific light source for detection is different from the light for the injury therapy. The surface may also be illuminated by the same light source used for the injury therapy. For example, a broadband light source, like the Welch Allyn reflectorized lamp assembly (part number 7103-001), may be used to illuminate the surface near the injury.
  obtaining a spectrum of light reflected from the surface. Oxy-hemoglobin has a absorption spectra at 542 and 580 nm, whereas Meth-hemoglobin has a absorption spectra at 630 nm. When Nitric Oxide is released from bound form to diffuse into the surrounding injury, a shift of absorption spectra from 630 nm to 542/580 nm occurs. The light reflected from the surface may be collected by fiber-optic cables and directed towards a micro-spectrometer sensitive to light in the wavelength range (500-700 nm).
  analyzing a ratio between a Meth-hemoglobin level and an Oxy-hemoglobin level according to the spectrum.
  calculating the Meth-hemoglobin level based on the ratio between the Meth-hemoglobin level and the Oxy-hemoglobin level.

In a further embodiment, the monitoring unit 21 may be further intended to detect the Meth-hemoglobin by:
  illuminating a surface near the injury. The surface may be illuminated by a specific light source used for detecting Meth-hemoglobin, and the specific light source used as the detection light is different from the light for the injury therapy. The surface may also be illuminated by the same light source as that used for injury therapy.
  obtaining a wave band of light reflected from the surface.
  detecting current of light reflected from the surface by converting the light reflected from the surface into current. This can be achieved by a plurality of photodiodes. The photodiodes are predefined as sensitive to three peaks 542 nm, 580 nm and 630 nm.
  analyzing a ratio between a Meth-hemoglobin level and an Oxy-hemoglobin level according to the current. The Oxy-hemoglobin peaks at 542 nm and 580 nm are identified, and the intensity of Oxy-hemoglobin is compared against the Meth-hemoglobin peak at 630 nm. The ratio of the peaks are then calculated and compared against a predefined model.
  calculating the Meth-hemoglobin level based on the ratio between the Meth-hemoglobin level and the Oxy-hemoglobin level.

Figure 3:
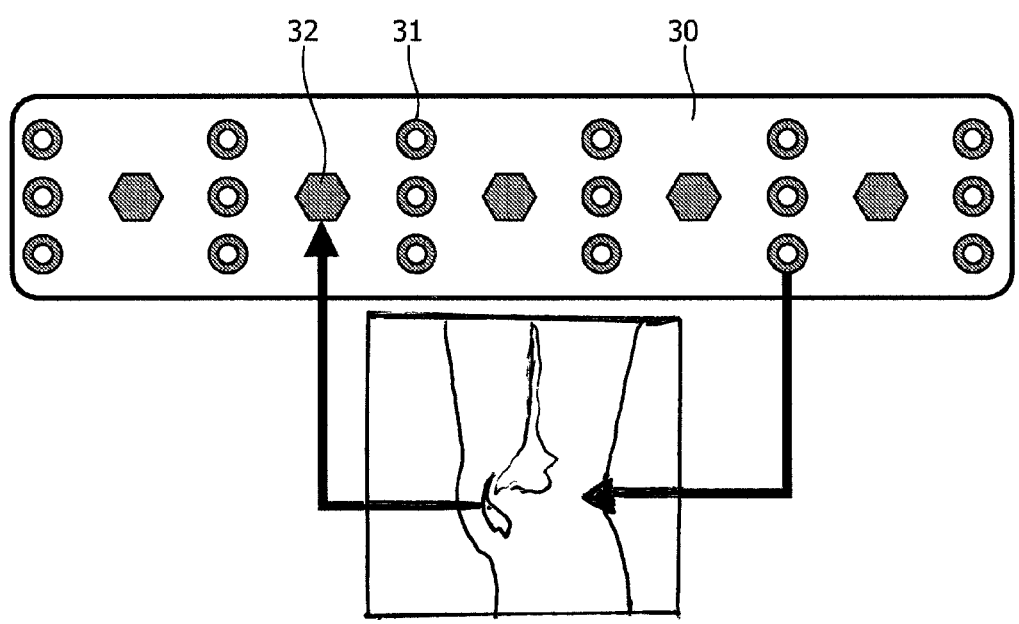
FIG. 3 depicts an injury therapy device in accordance with an embodiment of the invention.

FIG. 3 depicts an injury therapy device in accordance with an embodiment of the invention. The therapy device 30 comprises a plurality of light sources 31 and the apparatus 20 (not shown in FIG. 3). The apparatus 20 comprises the monitoring unit 21, the generating unit 22, and the adjusting unit 23. In one embodiment of the invention, the monitoring unit 21 may also comprise a plurality of the sensors 32 arranged together with the plurality of light sources 31.

The light source 31 may be LEDs (Light Emitting Diode) for emitting light on an injury for therapy. The monitoring unit 21 is used to monitor the Nitric Oxide level of the injury, so as to adjust dosage of light. According to the controlling signal from the generating unit 22, the adjusting unit 23 is intended to adjust the dosage of the light for therapy by adjusting the total intensity of the light, e.g. turning off/on one or more light source, adjusting intensities of one or more lights, or adjusting the intensities of all lights.

The sensors 32 are used for collecting information of an injury for the monitoring unit 21.

The light sources 31 and the sensors 32 are placed on a base (not labeled). The base is flexible to adjust to any part of body. The injury therapy device 30 can be used by patient at home or work and does not need expert intervention. The apparatus 20 may be supported by one or more CPUs (Central Processing Units) and/or control circuits, so as to adjust the dosage of the lights emitted from the light sources 31. The light sources 31 are powered by battery source or other elements.

Figure 4A:
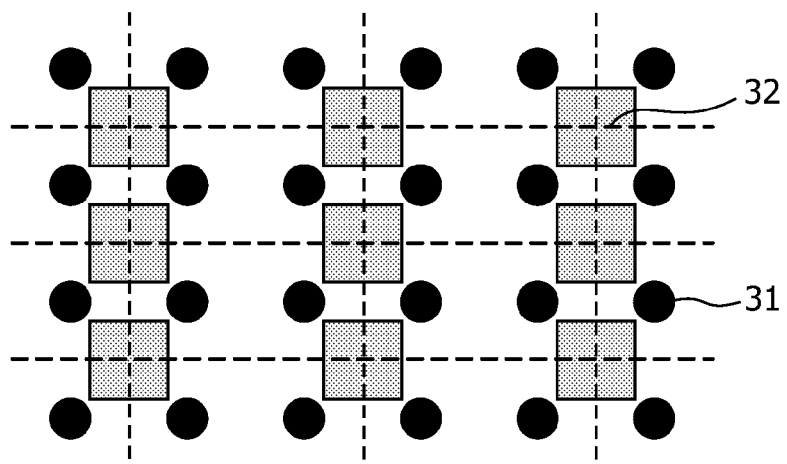
FIG. 4 depicts an injury therapy device in accordance with another embodiment of the invention.
Figure 4B:
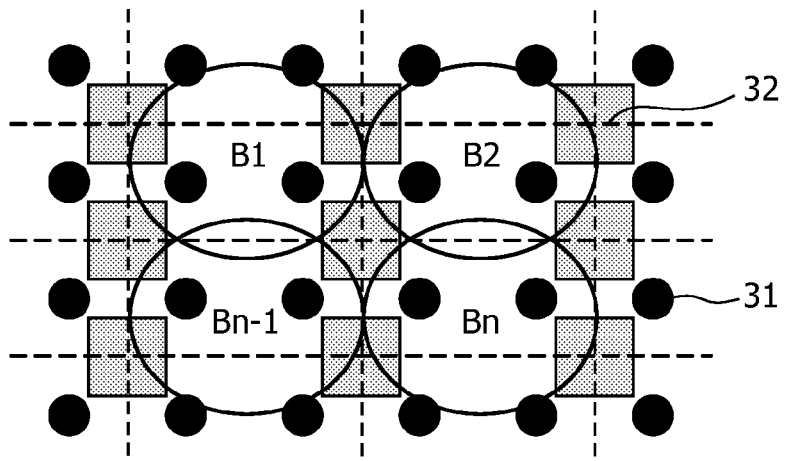
Figure 4C:
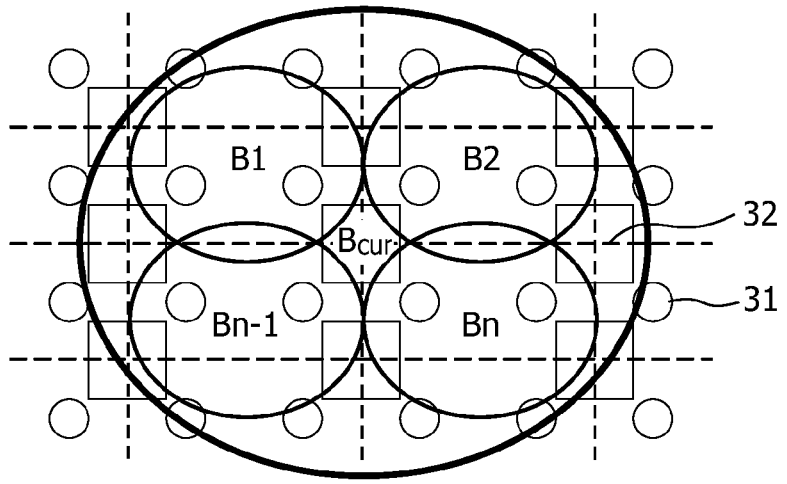

FIG. 4 depicts an injury therapy device in accordance with another embodiment of the invention. In FIG. 4, (A) depicts the composition of the LED and GMR sensors in the device; (B) depicts measuring magnetic field by each GMR sensor; (C) depicts a combination of the magnetic fields from all the GMR sensors.

The therapy device 30 comprises a plurality of light sources 31 and the apparatus 20 (not shown in FIG. 3). The apparatus 20 comprises the monitoring unit 21, the generating unit 22, and the adjusting unit 23. In one embodiment of the invention, the monitoring unit 21 may also comprise a plurality of the sensors 32 arranged together with the plurality of light sources 31.

The sensors 32 are Giant Magneto Resistive (GMR) sensors for detecting the magnetic field. The GMR sensors are more sensitive than the Hall-effect sensors. The sensors 32 consist of three by three arrays. An analog multiplexer (not shown in FIG. 4) may be used to select the signals from the nine sensors 32 for further signal conditioning, amplification, and analog to digital conversion.

The light sources 31 can emit lights in the infrared range approximately around 890 nm.

Before an injury therapy, the apparatus 20 computes an initial magnetic field ($B_{in}$); when the therapy starts, the apparatus 20 periodically computes the magnetic field ($B_{cur}$), and the $B_{cur}$ is higher than the $B_{in}$, so as to monitor the Nitric Oxide level.

$$B_{cur} = \sum_{i=1}^{n} B_i;$$

wherein i is equal to 1 to n, i represents the number of GMR sensors.

It should be noted that the above-mentioned embodiments illustrate rather than limit the invention and that those skilled in the art will be able to design alternative embodiments without departing from the scope of the appended claims. In the claims, any reference signs placed between parentheses shall not be construed as limiting the claim. The word "comprising" does not exclude the presence of elements or steps not listed in a claim or in the description. The word "a" or "an" preceding an element does not exclude the presence of a plurality of such elements. The invention can be implemented by unit of hardware comprising several distinct elements and by unit of a programmed computer. In the system claims enumerating several units, several of these units can be embodied by one and the same item of hardware or software. The usage of the words first, second and third, et cetera, does not indicate any ordering. These words are to be interpreted as names.

The invention claimed is:

1. A method of controlling a light for therapy of an injury of a subject, comprising the acts of:
    detecting a meth-hemoglobin level and a oxy-hemoglobin level of the subject at an injury site of the injury of the subject;
    after the detecting act, calculating a nitric oxide level according to a ratio between the meth-hemoglobin level and the oxy-hemoglobin level of the subject;
    after the calculating act, generating by a processor a controlling signal by comparing the nitric oxide level with a predefined threshold; and
    after the generating act, adjusting a dosage of the light provided to the injury site from a light source according to the controlling signal for providing the therapy.

2. The method as claimed in claim 1, wherein the detecting act includes acts of:
    detecting a magnetic field formed due to a transition from $Fe^{2+}$ to $Fe^{3+}$;
    acquiring an $Fe^{3+}$ level based on the detected magnetic field; and
    calculating the meth-hemoglobin level according to the $Fe^{3+}$ level.

3. The method as claimed in claim 1, wherein the detecting act includes acts of:
    illuminating a surface near the injury;
    obtaining a spectrum of light reflected from the surface;
    determining the ratio between the meth-hemoglobin level and the oxy-hemoglobin level according to the spectrum; and
    calculating the meth-hemoglobin level based on the ratio between the meth-hemoglobin level and the oxy-hemoglobin level.

4. The method as claimed in claim 1, wherein the detecting act includes acts of:
    illuminating a surface near the injury with the light from the light source;
    obtaining a wave band of light reflected from the surface;
    detecting a current for the light reflected from the surface by converting the light reflected from the surface into current;
    determining the ratio between a meth-hemoglobin level and an oxy-hemoglobin level according to the current; and
    calculating the meth-hemoglobin level based on the ratio between the meth-hemoglobin level and the oxy-hemoglobin level.

5. The method as claimed in claim 1, wherein the adjusting act increases the dosage of the light if the calculated nitric oxide level is higher than the predefined threshold, and decreases the dosage of the light if the calculated nitric oxide level is lower than the predefined threshold.

6. An apparatus for controlling a light for therapy of an injury of a subject, comprising:
    a light source configured to provide a dosage of the light for the therapy at an injury site of the injury;
    a monitoring unit configured to detect a meth-hemoglobin level and a oxy-hemoglobin level of the subject at the injury site; and
    a processor configured to:
    calculate a nitric oxide level according to a ratio between the meth-hemoglobin level and the oxy-hemoglobin level of the subject,
    generate a controlling signal by comparing the nitric oxide level with a predefined threshold, and
    adjust the dosage of the light for the therapy provided to the injury site from the light source according to the controlling signal for providing the therapy.

7. The apparatus as claimed in claim 6, wherein the monitoring unit is further configured to:
    detect a magnetic field formed due to a transition from $Fe^{2+}$ to $Fe^{3+}$, acquire an $Fe^{3+}$ level according to the magnetic field, and calculate the meth-hemoglobin level according to the $Fe^{3+}$ level.

8. The apparatus as claimed in claim 6, wherein monitoring unit is further configured to:
    illuminate a surface near the injury with the light from the light source;
    obtain a spectrum of light reflected from the surface;
    determine the ratio between a meth-hemoglobin level and an oxy-hemoglobin level according to the spectrum; and
    calculate the meth-hemoglobin level based on the ratio of the meth-hemoglobin level and the oxy-hemoglobin level.

9. The apparatus as claimed in claim 6, wherein the monitoring unit is further configured to:
    illuminate a surface near the injury;
    obtain a wave band of light reflected from the surface;
    detect a current for the light reflected from the surface by converting the light reflected from the surface into the current;
    determine the ratio between the meth-hemoglobin level and the oxy-hemoglobin level according to the current; and
    calculate the meth-hemoglobin level based on the ratio between the meth-hemoglobin level and the oxy-hemoglobin level.

10. The apparatus as claimed in claim 6, wherein the processor is further configured to increase the dosage if the nitric oxide level is higher than the predefined threshold, and decrease the dosage if the nitric oxide level is lower than the predefined threshold.

11. An injury therapy device comprising a plurality of light sources configured to emit lights for therapy of an injury of a subject and an apparatus for controlling a dosage of the lights from the light sources, wherein the apparatus comprises:
    a monitoring unit configured to indirectly monitor at an injury site a nitric oxide level released from the injury site of the injury; and
    a processor configured to:
    calculate a nitric oxide level according to a ratio between the meth-hemoglobin level and the oxy-hemoglobin level of the subject,
    generate a controlling signal by comparing the nitric oxide level with a predefined threshold, and
    adjust the dosage of the light for the therapy of the injury provided from the plurality of light sources according to the controlling signal,
    wherein the monitoring unit comprises a plurality of sensors configured to collect information from the injury, the information comprising one of magnetic field information and spectrum information.

12. The injury therapy device as claimed in claim 11, wherein the plurality of sensors are arranged together with the plurality of light sources on a base to collect the information from the injury.

13. The injury therapy device as claimed in claim 12, wherein the sensors are Giant Magneto Resistive sensors.

14. The injury therapy device of claim 11, wherein the monitoring unit indirectly monitors the nitric oxide level by detecting a meth-hemoglobin level and an oxy-hemoglobin level of the subject at the injury site.

15. The injury therapy device of claim 14, wherein the monitoring unit detects the meth-hemoglobin level by detecting a magnetic field formed due to a transition from $Fe^{2+}$ to $Fe^{3+}$, and acquiring an $Fe^{3+}$ level based on the detected magnetic field; and wherein the processor calculates the meth-hemoglobin level according to the $Fe^{3+}$ level.

16. The injury therapy device of claim 14, wherein the monitoring unit detects the meth-hemoglobin level by obtaining a spectrum of light reflected from a surface near the injury illuminated by the lights from the plurality of light sources, and the wherein the processor determines the ratio between the meth-hemoglobin level and the oxy-hemoglobin level according to the spectrum and calculates the meth-hemoglobin level based on the ratio between the meth-hemoglobin level and the oxy-hemoglobin level.

17. The injury therapy device of claim 14, wherein the monitoring unit detects the meth-hemoglobin level by obtaining a wave band of light reflected from a surface near the injury illuminated by the lights from the plurality of light sources, and the wherein the processor:

detects a current for the light reflected from the surface by converting the light reflected from the surface into the current;

determines the ratio between the meth-hemoglobin level and the oxy-hemoglobin level according to the current; and calculates the meth-hemoglobin level based on the ratio between the meth-hemoglobin level and the oxy-hemoglobin level.

18. The injury therapy device of claim 11, wherein the processor increases the dosage of the light if the nitric oxide level is higher than a predefined threshold, and decreases the dosage of the light if the nitric oxide level is lower than the predefined threshold.

* * * * *